United States Patent

Marlin

[11] Patent Number: 5,919,966
[45] Date of Patent: Jul. 6, 1999

[54] PROCESS FOR THE PREPARATION OF SPIRO BIS-PHOSPHITES

[75] Inventor: Gary Marlin, Morgantown, W. Va.

[73] Assignee: General Electric Company, Pittsfield, Mass.

[21] Appl. No.: 09/048,369

[22] Filed: Mar. 26, 1998

[51] Int. Cl.[6] .................................................. C07F 9/6574
[52] U.S. Cl. .................................................................. 558/78
[58] Field of Search ................................................ 558/78

[56] References Cited

U.S. PATENT DOCUMENTS

| | | |
|---|---|---|
| 3,039,993 | 6/1962 | Friedman . |
| 3,056,823 | 10/1962 | Hechenbleikner . |
| 3,281,381 | 10/1966 | Hechenbleikner . |
| 3,281,506 | 10/1966 | Shepard et al. . |
| 3,305,526 | 2/1967 | Guttag . |
| 3,342,767 | 9/1967 | Buckley . |
| 3,415,906 | 12/1968 | Shepard et al. . |
| 3,441,633 | 4/1969 | Friedman . |
| 3,467,733 | 9/1969 | Dever . |
| 3,482,002 | 12/1969 | Dever . |
| 3,488,407 | 1/1970 | Schall . |
| 3,558,554 | 1/1971 | Kurlyama . |
| 3,845,168 | 10/1974 | Guttag . |
| 4,024,049 | 5/1977 | Shell et al. . |
| 4,067,903 | 1/1978 | Hoch et al. . |
| 4,086,304 | 4/1978 | Hutton et al. . |
| 4,196,117 | 4/1980 | Spivack . |
| 4,237,075 | 12/1980 | Gough . |
| 4,276,233 | 6/1981 | Markezich et al. . |
| 4,312,818 | 1/1982 | Maul et al. . |
| 4,318,845 | 3/1982 | Spivack et al. . |
| 4,322,530 | 3/1982 | Jachimowicz . |
| 4,371,647 | 2/1983 | Minagawa et al. . |
| 4,391,761 | 7/1983 | Block et al. . |
| 4,407,765 | 10/1983 | Hardy . |
| 4,440,696 | 4/1984 | Maul et al. . |
| 4,492,661 | 1/1985 | Maul et al. . |
| 4,656,302 | 4/1987 | Dressler . |
| 4,705,879 | 11/1987 | Dressler . |
| 4,724,056 | 2/1988 | Doane . |
| 4,786,329 | 11/1988 | Chang et al. . |
| 4,882,374 | 11/1989 | Wang et al. . |
| 4,894,481 | 1/1990 | Burt . |
| 5,126,475 | 6/1992 | Bahrmann et al. . |
| 5,141,975 | 8/1992 | Enlow . |
| 5,235,086 | 8/1993 | Maul et al. . |
| 5,254,709 | 10/1993 | Hunter . |
| 5,371,263 | 12/1994 | Quotschalla et al. . |
| 5,424,348 | 6/1995 | Mahood . |
| 5,438,086 | 8/1995 | Stevenson et al. . |
| 5,468,895 | 11/1995 | Mahood . |
| 5,534,645 | 7/1996 | Quotschalla et al. . |

*Primary Examiner*—Michael G. Ambrose

[57] ABSTRACT

A process for producing organo-phosphites of the formula

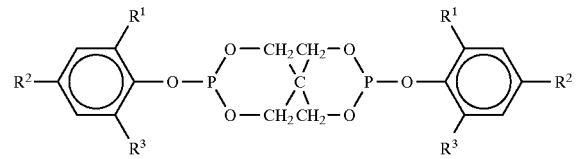

wherein $R^1$ and $R^2$ are each 2,4-di-tert-butyl and $R^3$ is hydrogen is provided. The process involves heating a mixture of a pentaerythritol bis-phosphorohalidite and a phenolic compound and applying a vacuum of at least about 10 inches of mercury wherein the temperature of the reaction mixture is maintained between about 30° C. and about 140° C. Conversions to the organic spiro bis-phosphite is at least twice that of the same process without a vacuum.

24 Claims, No Drawings

PROCESS FOR THE PREPARATION OF SPIRO BIS-PHOSPHITES

FIELD OF THE INVENTION

This invention relates to a process for the preparation of organic phosphites, specifically spiro bis-phosphites. In an especially preferred embodiment, this invention relates to a process to prepare bis(dialkylphenyl)pentaerythritol diphosphites.

BACKGROUND OF THE INVENTION

Organic phosphites are used in the stabilization of a wide variety of polymeric systems. Many different phosphites have been proposed for use either alone or in combination with other stabilizers. Such phosphites and their utilities are described in U.S. Pat. Nos. 4,371,647, 4,656,302, 4,705,879, 5,126,475, 5,141,975, and 5,438,086. The importance of organic phosphites as stabilizers has lead to the development of a variety of specialty organic phosphites that have enhanced effectiveness for stabilization.

Sterically hindered organic phosphites, and in particular diphosphites based upon pentaerythritol and containing alkyl, aryl, or alkyl-substituted aryl groups wherein the substitution is selected from the group consisting of t-butyl, t-amyl, t-hexyl, cyclohexyl, t-pentyl, and t-octyl, are especially desirable compounds due to their enhanced hydrolytic stability, ease of handling and compatibility with a wide variety of polymeric systems. The bis(2,4-di-tertbutylphenyl)pentaerythritol diphosphites are also especially preferred for their improved hydrolytic stability over other alkyl substituted phosphites as well as their enhanced compatibility with some polymeric resins, especially polyolefins.

The organic diphosphites are generally prepared using methods involving reactions between the appropriate hydroxy compounds and phosphorous trihalides, e.g., phosphorous trichloride. Such methods and other useful methods are described in U.S. Pat. Nos. 3,839,506, 4,116,926, 4,290,976, 4,440,696, and 4,492,661. The ease of substitution of the halides on the phosphorous trihalide decreases as each halide is replaced. For example, in the preparation of bis(aryl)pentaerithritol diphosphites, the pentaerithritol hydroxyls readily react with a phosphorous trihalide to yield a bis(disubstituted halo phosphite (i.e., an intermediate di-substituted diphosphorohalidite). The displacement of the third halo group is less than quantitative and is considerably slower in rate. Additionally, displacement of the third halo group by a sterically hindered phenol is even more difficult and requires elevated temperatures and/or use of a catalyst.

In order to increase the rate of reaction and the degree of completion for displacing the third halide with a sterically hindered moiety, various techniques have been generally utilized in the art. These techniques include: elevating the reaction mixture temperature and use of hydrogen halide acceptors, e.g., amines. Such techniques are described in U.S. Pat. Nos. 3,281,506, 4,237,075, 4,312,818, 4,440,696, and 4,894,481.

Generally in the case of diphosphites derived from pentaerythritol, the procedures of the prior art result in undesirable product mixtures including caged structures wherein three of the hydroxyls on a single pentaerythritol have reacted with one phosphorous trihalide. Additionally, various polyphosphite compounds are also formed leading to low conversions to the desired product. The resulting phosphite mixture containing a halo-phosphite is extremely difficult to purify and the residual halo-phosphite can lead to acid impurities that affect the long term stability of the desired organic phosphite. It is therefore apparent that a need continues to exist for improved processes for the preparation of bis(dialkylphenyl)pentaerythritol diphosphites, and especially bis(2,4-di-tertbutylphenyl)pentaerythritol diphosphite, that overcome the aforementioned difficulties.

SUMMARY OF THE INVENTION

The present invention relates to a new process for the production of organic spiro bis-phosphites from bis-(halophosphites) and hydroxyl-containing compounds, preferably sterically hindered phenols, wherein vacuum has been utilized to drive the esterification reaction between the bis-(halophosphites) and hydroxyl-containing compounds.

In a first embodiment of the present invention, the bis-(halophosphite) is of the general formula:

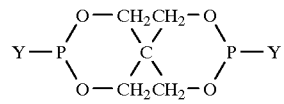

wherein Y is a halogen or other good leaving group.

In a second embodiment of the present invention, the bis-(halophosphite) is of the general formula:

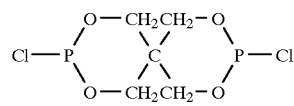

In a third embodiment of the present invention, the hydroxyl-containing compound is a phenol of the general formula:

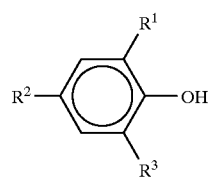

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl.

In a fourth embodiment of the present invention, the hydroxyl-containing compound is a phenol of the general formula:

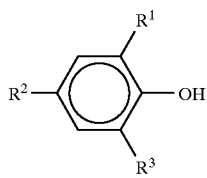

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl with the proviso that at least one of $R^1$ and $R^2$ is t-butyl, t-amyl, t-hexyl, cyclohexyl, cumyl, t-pentyl, or t-octyl.

In a fifth embodiment of the present invention, the hydroxyl-containing compound is a phenol of the general formula:

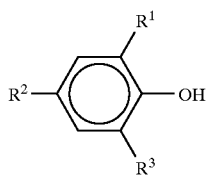

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl with the proviso that at least one of $R^1$ and $R^2$ is t-butyl, t-amyl, t-hexyl, cyclohexyl, cumyl, t-pentyl, or t-octyl, and $R^3$ is hydrogen.

In a sixth embodiment of the present invention, the hydroxyl-containing compound is 2,4-di-tertbutylphenol and bis-(halophosphite) is of the general formula:

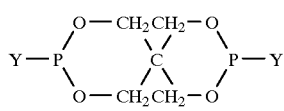

wherein Y is a halogen, preferably chlorine, or another good leaving group.

In a seventh embodiment of the present invention, the organic spiro bis-phosphite is of the formula:

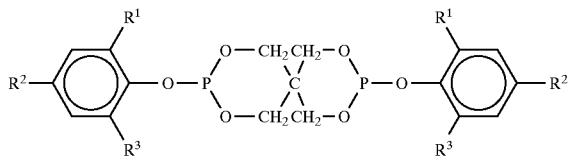

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl.

In a eighth embodiment of the present invention, the organic spiro bis-phosphites is of the formula:

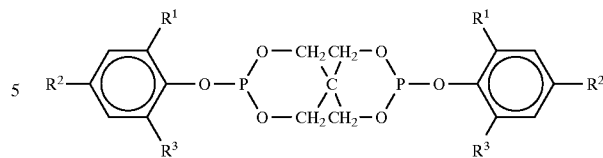

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl with the proviso that at least one of $R^1$ and $R^2$ is t-butyl, t-amyl, t-hexyl, cyclohexyl, cumyl, t-pentyl, or t-octyl.

In an ninth embodiment of the present invention, the organic spiro bis-phosphites is of the formula:

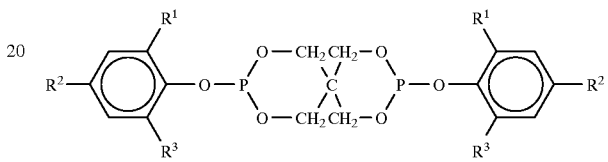

wherein each $R^1$ and $R^2$ is independently selected from the group consisting of methyl, ethyl, n-propyl, iso-propyl, n-butyl, t-butyl, t-amyl, t-hexyl, cyclohexyl, cumyl, t-pentyl, and t-octyl, and $R^3$ is hydrogen.

In an tenth embodiment of the present invention, the organic spiro bis-phosphites is of the formula:

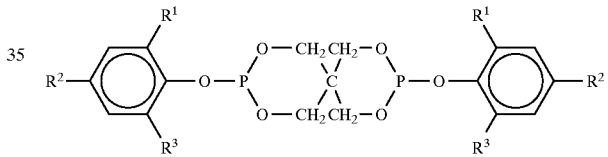

wherein each $R^1$ and $R^2$ is t-butyl and $R^3$ is hydrogen.

In an eleventh embodiment of the present invention, a vacuum of at least 15 inches of mercury is applied to esterification reaction between the bis-(halophosphite) and hydroxyl-containing compound.

In a twelfth embodiment of the present invention, a vacuum of at least 25 inches of mercury is applied to esterification reaction between the bis-(halophosphite) and hydroxyl-containing compound.

In a thirteenth embodiment of the present invention, the reaction mixture containing the bis-(halophosphite) and hydroxyl-containing compound is substantially free of esterification catalysts.

In a fourteenth embodiment of the present invention, the converion of the organic spiro bis-phosphites of the formula:

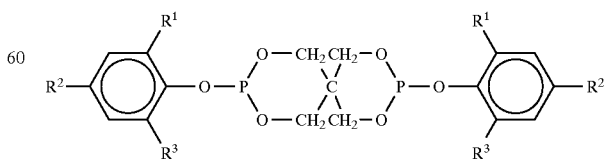

wherein each $R^1$ and $R^2$ is independently selected from the group consisting of methyl, ethyl, n-propyl, iso-propyl, n-butyl, t-butyl, t-amyl, t-hexyl, cyclohexyl, cumyl, t-pentyl, and t-octyl, and $R^3$ is hydrogen results in a yield of at least about 84%.

In a fifteenth embodiment of the present invention, the conversion to the organic spiro bis-phosphites from the bis-(halophosphites) and hydroxyl-containing compound is done at less than about 140° C.

In a sixteenth embodiment of the present invention, the reaction mixture containing the bis-(halophosphite) and hydroxyl-containing compound is substantially free of esterification catalysts and is maintained at a temperature of less than about 80° C.

These and other embodiments of the present invention will become apparent to those skilled in the art with the disclosure of the present invention.

DETAILED DESCRIPTION OF THE INVENTION

The present invention relates to processes to produce organic spiro bis-phosphites is of the formula:

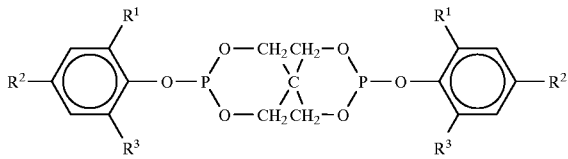

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl. In general, organic phosphites are typically produced by reacting a phosphorous trihalide, e.g., phosphorous trichloride, with hydroxyl-containing compounds wherein the halides are displaced on the phosphorous trihalide by the hydroxyl-containing compounds. The ease of substitution by the hydroxyl-containing compounds depends at least partly on the steric bulk of the hydroxyl-containing compounds. When the hydroxyl-containing compound has a low steric demand (i.e. the hydroxyl-containing compound is not a sterically hindered hydroxyl-containing compound), the displacement of the halides is somewhat statistical. However, as the steric demand of the hydroxyl-containing compound increases, increased selectivity may be obtained to achieve less substituted halophosphites. In displacement of the first two halides on the phosphorous trihalide, the reactions are generally facile and proceed to completion without the need for catalysis regardless of the steric limitations of the hydroxyl-containing compound.

In the displacement of the third halide moiety from the di-substituted phosphorus halide, the degree of conversion to the tri-substituted phosphite is adversely affected by steric considerations of both the di-substituted phosphorus halide and the hydroxyl-containing compound. Catalysts, including amines, are often employed in the art to increase the degree of conversion to the tri-substituted phosphite. Unfortunately, amine catalysts result in amine halide salt impurities in the desired spiro bis-phosphite compound and purification steps must be undertaken to remove the salt.

Elevating the reaction mixture is also known in the art to assist in driving the reaction towards completion. In the case of spiro bis-phosphites derived from pentaerythritol, elevating the temperature above about 80° C. leads to increases in the level of byproducts of the general formulas:

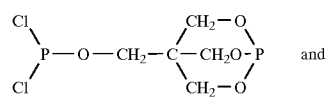

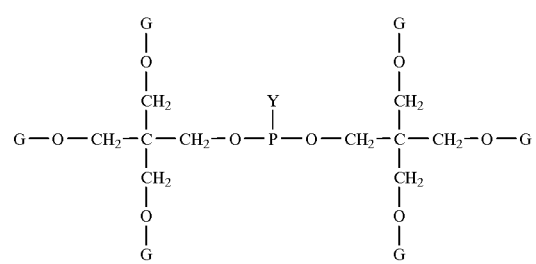

wherein Y is halogen or another good leaving group and each G can independently be a phosphorous or hydrogen increases as the temperature is increased. When G is a phosphorous, various polyphosphite compounds are possible. These byproducts and other similar by-products are difficult to remove from the desired spiro bisphosphite compound and accordingly are extremely undesirable.

It was quite surprising to discover that the use of vacuum can readily drive the esterification reaction between the bis-(halophosphite) of the general formula:

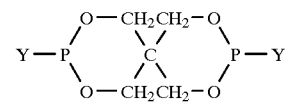

wherein Y is a halogen, preferably chlorine, or another good leaving group and the phenol of the general formula:

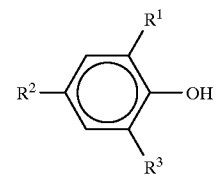

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl.

Generally with organic phosphites, the displacement of the third halide is considerably slower than the displacement of the other halides, however, the displacement commonly proceeds to afford high conversions to the tris-substituted organo-substituted phosphite. In the case of the pentaerythritol dichloro diphosphite, the reaction with 2,4-di-tertbutylphenol is extremely sluggish and proceeds only to about 30% completion after more than 10 hours when neither vacuum nor catalyst are utilized. Surprisingly, under the same reaction conditions, applying a vacuum of at least about 10 inches of mercury, preferably of at least about 15 inches of mercury, and most preferably of at least about 20 inches of mercury, to the reaction mixture leads to at least about 75% conversion in about 8 hours. The magnitude of the increase in the conversion is quite surprising when compared to a control that does not utilize vacuum. Moreover, the high conversions can be achieved without the use of amine catalysts and the concomitant amine halide salts that must be removed from the product. It is also possible to use a combination of vacuum and catalyst to achieve even higher and faster conversions albeit with the necessity of removing the catalyst by-product. It should be clear that in a preferred embodiment of the present invention, the esterification reaction is carried out substantially free of, and more preferably, free of esterification catalysts.

The reaction between pentaerythritol and phosphorus trihalide to form an intermediate pentaerythritol bis-phosphorohalidite may be carried out with or without the use of a solvent. Typically $PCl_3$ is utilized although other phosphorus halides or derivatives may be used. Generally, $PCl_3$ is added to the pentaerythritol or alternatively, the pentaerythritol can be added to $PCl_3$. Preferably the $PCl_3$ is added to the pentaerythritol with the reaction mixture being maintained at a temperature of about 5° to 50° C. The reaction is exothermic in the absence of a solvent, but a temperature moderating effect is produced by the cooling effect of vigorous HCl evolution. Hence, by effective control of the addition of $PCl_3$, the reaction may be made self-regulating in the temperature range of between about 5° to 15° C. A slower addition favors lower temperatures and it is preferred to cool the reaction mixture during the addition. Control of reaction temperature helps to minimize the aforementioned by-products. A slight excess of stoichiometric amounts of $PCl_3$ is commonly utilized.

When a solvent is utilized, it is important that the solvent be neutral to the reaction ingredients and by-products. Typical solvents include, for example, toluene, heptane, xylene, methylene chloride, chloroform, and benzene as well as hydrocarbon solvents such as ISOPAR and NORPAR. Preferred solvents are methylene chloride, heptane, or xylene. The level of solvent can vary widely depending on a number of variables including, for example, the reactor design and stirring capability. Determination of an exact amount of solvent is readily determined without undue experimentation.

This reaction can be driven to completion and the residual halide by-product, such as HCl, may optionally be removed by gently raising the temperature of the product to room temperature to about 50° C. Any solvent utilized is generally at least partially removed, typically by application of a vacuum, to insure complete removal of the hydrogen halide by-product to yield an intermediate pentaerythritol bis-phosphorohalidite product.

The intermediate pentaerythritol bis-phosphorohalidite product is next allowed to react with a hydroxy-substituted compound to yield the desired trisubstituted organic phosphite. The reaction between the intermediate pentaerythritol bis-phosphorohalidite product and the hydroxy-substituted compound may be conducted in the same reaction vessel that was employed to produce the intermediate phosphorohalidite by merely introducing the hydroxy-substituted compound followed by applying the vacuum to the reactor. Additionally, the color of the final phosphite product can be controlled by the addition rate of the intermediate pentaerythritol bis-phosphorohalidite product, with a slower addition rate leading to less color in the final phosphite product. An appropriate addition rate can be readily determined by color determination of the final product and depends also on factors such as the exact reaction conditions, ratios of ingredients, and equipment utilized. Regardless of the order of addition, the reaction is generally carried out at a suitable temperature between about 20 to about 175° C. and preferably between about 60° to about 155° C. The pressure of the reaction system is maintained at a vacuum of at least about 10 inches of mercury, preferably of at least about 15 inches of mercury, and most preferably of at least about 25 inches of mercury to atmospheric pressure. The purpose of the vacuum is believed to be to assist in removal of the hydrogen chloride from the reaction mixture during the esterification reaction. Typical reaction times to substantial completion are up to about 24 hours. Preferably, the temperature and pressure conditions are selected to afford the maximum amount of product within a time period of about 8 to about 12 hours.

It is during the reaction of the pentaerythritol bis-phosphorohalidite and the hydroxy-substituted compound that when an amine catalyst is utilized that the corresponding ammonium hydrogen chloride salt is formed between the polymeric amine and the hydrogen chloride by-product (chloride is described herein as $PCl_3$ is the most often used starting halophosphite). Another unexpected advantage of using vacuum is that the salt is eliminated from the reaction mixture which also is advantage from a process viewpoint. Therefore, it should be clear that the present invention includes a process that is substantially, and preferably free of amine catalyst.

The final proportions of reactants are at least approximately stoichiometric. It is often desirable to work with at least a slight stoichiometric excess of one of the reactants to help drive the reaction as for to completion as possible. It is often beneficial to employ a molar ratio of 2.0 or greater of the phenolic compound to the bis-(halophosphite). In a preferred embodiment, the ratio of phenolic compound to bis-(halophosphite) is in the range of about 2 to about 2.5 to 1.

The reaction product can be dissolved in an organic solvent and filtered to remove any solid materials. The solvent can be removed by flash distillation or another solvent removal technique or alternatively, the phosphite product can be isolated by crystallization or precipitation from an organic solvent. Typical organic solvents include hexane, heptane, octane, isopropyl alcohol, acetonitrile, toluene, NORPAR, ISOPAR, and the like. The phosphite product can also be purified using melt crystallization techniques or combinations of melt crystallization and solvent crystallization and/or precipitation.

When the phosphite stabilizer is isolated in crystalline form, the present invention contemplates that it may be utilized in solid amorphous form. The amorphous phosphite composition is formed by rapid cooling of melt of the phosphite. Such melt may be a mixture of the phosphite and polyamine which is rapidly cooled to form a solid amorphous phosphite composition. The amorphous nature of composition enhances the hydrolytic stability of the solid composition compared to crystalline composition containing the same constituents.

The phosphites made by the process of the present invention include all organic phosphites derived from pentaerithritol and a hydroxyl-containing compound that is a phenol of the general formula:

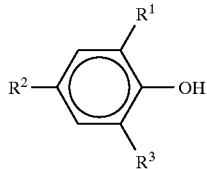

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl. Especially preferred phosphites, however, are sterically hindered spiro bis-phosphites wherein the hydroxyl-containing compound is a phenol of the general formula:

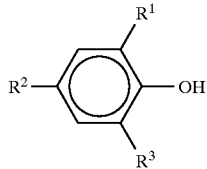

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl with the proviso that at least one of $R^1$ and $R^2$ is t-butyl, t-amyl, t-hexyl, cyclohexyl, cumyl, t-pentyl, or t-octyl, and $R^3$ is hydrogen. In the practice of the present invention, as especially preferred organic spiro bis-phosphites is of the formula:

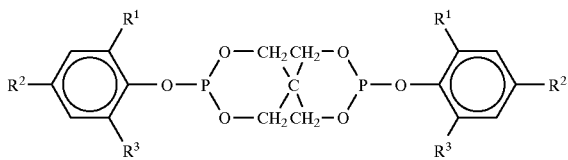

wherein each $R^1$ and $R^2$ is t-butyl and $R^3$ is hydrogen.

All patents cited by reference are incorporated herein by reference.

In order that those skilled in the art will be better able to practice the invention, the following examples are given by way of illustration and not by way of limitation.

EXAMPLES

General Procedure:

A reaction vessel was charged with 2,4-di-t-butylphenol (0.22 mol) with xylene (14 grams) and warmed to about 60° C. under an inert atmosphere. A bis-(halophosphite) of the general formula:

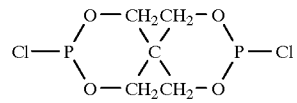

was added (0.10 mol in 26 grams of xylene) and the reaction mixture was maintained at about 60° to 80° C. for about 10 hours. The degree of product conversion to the tri-substituted phosphite was measured by gas chromotagraphy. The final phosphate was crystallized from acetonitrile or isopropyl alcohol. The resultant phosphite had the formula:

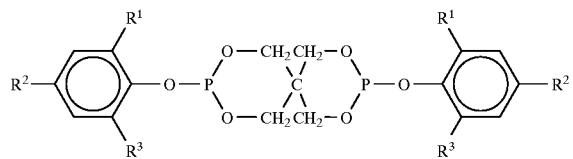

wherein each $R^1$ and $R^2$ is t-butyl and $R^3$ is hydrogen. The yield was 28.7% based upon the amount of bis-(halophosphite).

Vacuum Procedure:

The general procedure was carried out with the addition of a vacuum of about 25 inches of mercury was applied after addition of the bis-(halophosphite)/xylene solution. After about 8 hours, the same resultant phosphite was obtained with a yield of 76.5% based upon the amount of bis-(halophosphite).

The above example demonstrates the unexpectedly high conversion that can be obtained with the use of a vacuum applied to the reaction mixture. These results are unexpected because HCl is very volatile under the reaction conditions such that applying a vacuum would be expected to have little effect on the rate of conversion.

What is claimed:

1. A process to produce an organic spiro bis-phosphite, wherein said process comprises heating a reaction mixture containing a bis-(halophosphite) and a phenolic compound and applying a vacuum of at least about 10 inches of mercury to the reaction mixture.

2. The process of claim 1, wherein bis-(halophosphite) is of the general formula:

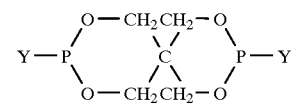

wherein Y is a halogen.

3. The process of claim 2, wherein the bis-(halophosphite) is of the general formula:

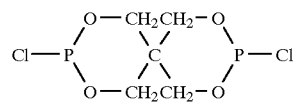

4. The process of claim 1, wherein phenolic compound is of the general formula:

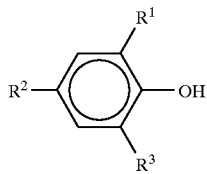

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl.

5. The process of claim 1, wherein the phenolic compound is of the general formula:

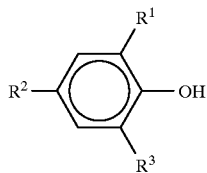

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl with the proviso that at least one of $R^1$ and $R^2$ is t-butyl, t-amyl, t-hexyl, cyclohexyl, cumyl, t-pentyl, or t-octyl, and $R^3$ is hydrogen.

6. The process of claim 1, wherein the phenolic compound is of the general formula:

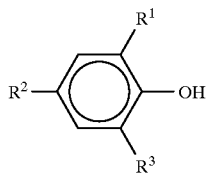

wherein each $R^1$ and $R^2$ is t-butyl and $R^3$ is hydrogen.

7. The process of claim 1, wherein the Spiro bis-phosphite is of the formula:

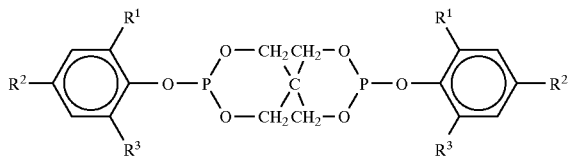

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl.

8. The process of claim 2, wherein the Spiro bis-phosphite is of the formula:

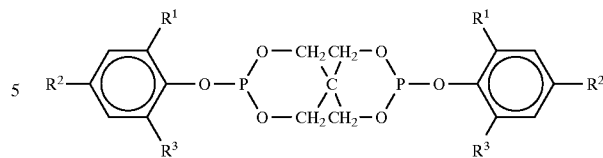

wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, cumyl, t-pentyl, and t-octyl with the proviso that at least one of $R^1$ and $R^2$ is t-butyl, t-amyl, t-hexyl, cyclohexyl, cumyl, t-pentyl, or t-octyl, and $R^3$ is hydrogen.

9. The process of claim 1, wherein the conversion to the organic phosphite is at least about 70%.

10. The process of claim 1, wherein the process further comprises heating the bis-(halophosphite) and the phenolic compound in a solvent.

11. The process of claim 1, wherein a vacuum of at least about 15 inches of mercury is applied to the reaction mixture.

12. The process of claim 1, wherein a vacuum of at least about 25 inches of mercury is applied to the reaction mixture.

13. A process to produce an organic spiro bis-phosphite of the formula

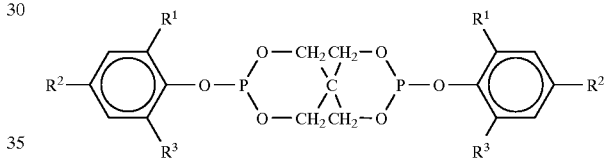

wherein $R^1$ and $R^2$ are each 2,4-di-tert-butyl and $R^3$ is hydrogen, wherein said process comprises heating a reaction mixture containing a bis-(halophosphite) of the formula:

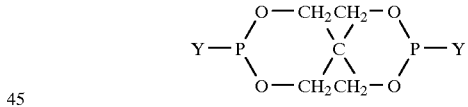

wherein Y is chlorine,
and a phenolic compound of the formula:

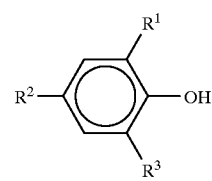

wherein each $R^1$ and $R^2$ is t-butyl and $R^3$ is hydrogen, and applying a vacuum of at least about 10 inches of mercury to the reaction mixture.

14. The process of claim 13, wherein the temperature of the reaction mixture is maintained between about 30° C. and about 140° C.

15. The process of claim 13, wherein a vacuum of at least about 15 inches of mercury is applied to the reaction mixture.

16. The process of claim 13, wherein the conversion to the organic spiro bis-phosphite is at least twice that of the same process without a vacuum when measured after about an 8 hour reaction time wherein the temperature of the reaction mixture is maintained between about 30° C. and about 140° C.

17. The process of claim 1, wherein the process is substantially free of esterification catalysts.

18. The process of claim 1, wherein the process is free of esterification catalysts.

19. The process of claim 1, wherein the process is substantially free of esterification catalysts and is maintained at a temperature of less than about 80° C.

20. The process of claim 1, wherein the process further comprises heating the bis-(halophosphite) and the phenolic compound in a solvent with an amine.

21. The process of claim 13, wherein the process is substantially free of esterification catalysts.

22. The process of claim 13, wherein the process is free of esterification catalysts.

23. The process of claim 13, wherein the process further comprises heating the bis-(halophosphite) and the phenolic compound in a solvent.

24. The process of claim 13, wherein the process further comprises heating the bis-(halophosphite) and the phenolic compound in a solvent with an amine.

* * * * *